US00PP28198P3

(12) United States Plant Patent
Olesen

(10) Patent No.: US PP28,198 P3
(45) Date of Patent: Jul. 18, 2017

(54) MINIATURE ROSE PLANT NAMED 'POULPAR088'

(50) Latin Name: ***Rosa* hybrid**
Varietal Denomination: Poulpar088

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 14/756,253

(22) Filed: Aug. 20, 2015

(65) Prior Publication Data

US 2017/0055392 P1 Feb. 23, 2017

(51) Int. Cl.
*A01H 5/02* (2006.01)

(52) U.S. Cl.
USPC ..... Plt./122

(58) Field of Classification Search
USPC ..... Plt./116, 122
See application file for complete search history.

(56) References Cited

PUBLICATIONS

"Perfection by Poulsen—Indoor Roses Main Varieties 2013," Jan. 2013 (3 pages total).*

* cited by examiner

*Primary Examiner* — Susan McCormick Ewoldt

(57) ABSTRACT

A new garden rose plant of the miniature class which has abundant, red flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar088'.

SUMMARY OF THE INVENTION

The present invention constitutes a new and distinct variety of garden rose plant which originated from a controlled crossing between the female seed parent, to an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar088', originated as a single seedling from the stated cross.

The new variety may be distinguished from its male pollen parent and female seed parent primarily by the following characteristics. The female seed parent has flowers which are 100 mm in diameter, while the new variety has flowers which are 60 mm in diameter. The male pollen parent has small flowers, 40 to 50 mm in diameter.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar088' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar088' was selected in the spring of 2008 by the inventor as a single plant from the progeny of the aforementioned hybridization.

Asexual reproduction of 'Poulpar088' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpar088' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar088'. Specifically illustrated are open flowers, a cluster of open flowers, petals detached, leaves, flower buds at various stages of opening, and reproductive flower parts. Plants shown are one year old.

DETAILED DESCRIPTION OF THE VARIETY

The following is a description of 'Poulpar088', as observed in its growth in in a field nursery in Marion County, Oreg. Observed plants are one year old, and were grown on their own roots. Color references are made using The Royal Horticultural Society (London, England) Colour Chart, 2001, except where common terms of color are used.

For a comparison, several physical characteristics of the rose variety 'Poulhappy', U.S. Plant Pat. No. 9,483 are compared to 'Poulpar088' in Chart 1.

CHART 1

| | 'Poulpar088' | 'Poulhappy' |
|---|---|---|
| Petal Count | 80 | 25-30 |
| Flower Diameter | 60 mm | 38 mm |
| Coloration of upper petal surface | Red Group 45A | Red Group 46B |

FLOWER AND FLOWER BUD

Blooming habit: Continuous.

Flower bud:

*Size.*—Upon opening, 25 mm in length from base of receptacle to end of bud. Bud diameter is 12 mm.

*Bud form.*—Ovoid.

*Bud color.*—As sepals divide petals are Red Group 46A.

*Sepal inner surface.*—Color: Yellow-Green Group 146D. Surface: Lightly pubescent.

*Sepal outer surface.*—Color: Yellow-Green Group 144A with strong intonations of Greyed-Purple Group 183A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 7 mm wide.

*Receptacle.*—Texture: Smooth. Size: 7 mm in height, 7 mm wide. Color: Yellow-Green Group 144A with intonations of Greyed-Purple Group 183A. Shape: Campanulate.

*Pedicel.*—Surface: Smooth. Length: 25 mm. Diameter: 3 mm on average. Color: Greyed-Purple Group 185A. Strength: Strong.

Flower bud development: Flower buds are borne in clusters of 3 to 5 flower buds per stem. The entire inflorescence diameter is about 120 mm.

Flower bloom:

*Fragrance.*—None.

*Duration.*—The blooms have a duration on the plant of approximately 20 days. Petals fall cleanly away from plant after flowers have fully matured.

*Size.*—Flower diameter is 60 mm when open. Flower depth is 20 mm.

*Flower shape.*—Quartered-rosette, very double, with many overlapping petals packed into quarter sections.

*Shape of flower, side view.*—The upper portion is flattened convex. The lower portion is concave.

Petalage: Under normal conditions, flowers have 80 petals total.

General tonality of flower: Open flowers are Red Group 45A.

Petal color:

*Upon opening, outer petals.*—Upper surface: Red Group 45A. Lower surface: Red Group 53B.

*Upon opening, inner petals.*—Upper surface: Red Group 45A. Lower surface: Red Group 53B.

*Basal petal spots, upon opening.*—Upper surface: Yellow Group 4A. Lower surface: Yellow Group 4A.

*After opening, outer petals.*—Upper surface: Red Group 45A. Lower surface: Red Group 53B.

*After opening, inner petals.*—Upper surface: Red Group 45A. Lower surface: Red Group 53B.

*Basal petal spots, after opening.*—Upper surface: Yellow Group 4A. Lower surface: Yellow Group 4A.

Petals:

*Petal reflex.*—Strong, bilateral.

*Margin.*—Entire and uniform. No undulations.

*Shape.*—Broad elliptical. Apex shape: Rounded. Base shape: Obtuse.

*Size.*—21 mm (l)×25 mm (w).

*Texture.*—Smooth.

*Thickness.*—Average.

Petaloids:

*Size.*—15 mm (l) by 8 mm (w).

*Quantity.*—About 10 to 15.

*Shape.*—Elliptical. The base is acute and the apex is rounded.

*Color.*—Upper surface is Red Group 45A. Lower surface is Red Group 53B. Yellow Group 4A petal spot on upper and lower surfaces.

Reproductive flower parts:

*Pollen.*—None observed.

*Anthers.*—Size: 1 mm in length. Color: Yellow Group 9B. Quantity: 40 on average.

*Filaments.*—Color: Yellow Group 4D. Length: 3 mm.

*Pistils.*—Length: 4 mm. Quantity: 25 on average.

*Stigmas.*—Color: Greyed-Yellow Group 160C.

*Styles.*—Color: Green-White Group 157A.

*Location of stigmas.*—Superior in location relative to the length of the filaments and the height of the anthers.

*Hips.*—None observed to date.

PLANT

Plant growth: Upright, bushy. Plants are 30 cm in height, and 25 cm wide.

Stems:

*Color.*—Juvenile growth: Yellow-Green Group 144A with strong intonations of Greyed-Purple Group 189A. Mature growth: Yellow-Green Group 146A.

*Length.*—On average, canes are 13 cm from the base of the plant to the flowering portion.

*Diameter.*—4 mm.

*Internodes.*—On mature canes about 20 mm between nodes.

*Surface texture.*—Young wood: Smooth. Older wood: Smooth.

Long prickles:

*Incidence.*—4 prickles per 10 cm of stem.

*Size.*—Average length of prickles on mature stems is 3 mm.

*Shape.*—Upper portion is linear. Lower portion is concave.

*Color.*—Juvenile prickles: Greyed-Red Group 181A. Mature prickles: Greyed-Red Group 181A.

Plant foliage:

*Compound leaf.*—100 mm (l)×60 (w).

*Quantity.*—3 to 4 leaves per 10 cm of stem on average.

*Color of juvenile foliage.*—Upper side: Yellow-Green Group 144A. Lower side: Yellow-Green Group 144B.

*Color of mature foliage*.—Upper side: Yellow-Green Group 147A. Lower side: Yellow-Green Group 147C.

Plant leaves and leaflets:

*Stipules*.—Size: 20 mm long, 10 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 2 mm.

*Upper surface*.—Color: Yellow-Green Group 147A.

*Lower surface*.—Color: Yellow-Green Group 146C.

*Rachis*.—Length: 35 mm. Upper surface: Color: Yellow-Green Group 147A with intonations of Greyed-Purple Group 187A.

*Lower surface*.—Color: Yellow-Green Group 146C. Observations: Small prickles

*Leaflet*.—Quantity: Normally 5 leaflets. Margins: Serrated. Size: On average terminal leaflets are 35 mm long, 22 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium sps*., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar088', substantially as illustrated and described herein, due to its abundant red flowers, disease resistance, and extended period of bloom.

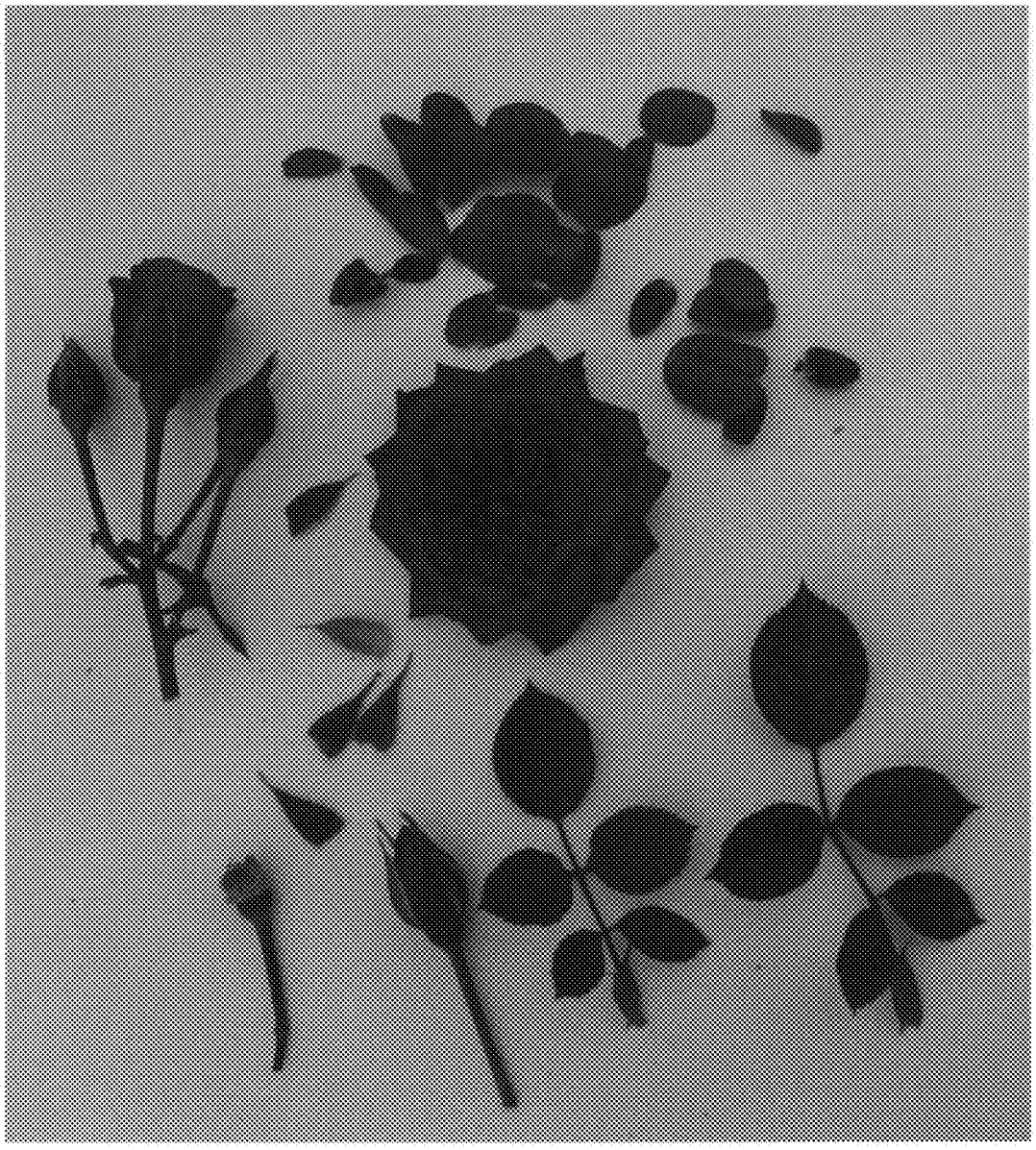

* * * * *